United States Patent
Bismuth et al.

(10) Patent No.: US 12,288,275 B2
(45) Date of Patent: Apr. 29, 2025

(54) METHODS AND SYSTEMS FOR BREAST TOMOSYNTHESIS

(71) Applicant: GE Precision Healthcare LLC, Waukesha, WI (US)

(72) Inventors: Vincent Bismuth, Yvelines (FR); Sylvain Bernard, Montigny le Bretonneux (FR); Fanny Patoureaux, Yvelines (FR); Yana Popova, Courbevoie (FR); Jorge Corsino Espino, Paris (FR); Xavier Mancardi, Yvelines (FR); Mathilde Ravier, Paris (FR)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 722 days.

(21) Appl. No.: 17/443,939

(22) Filed: Jul. 28, 2021

(65) Prior Publication Data

US 2023/0031814 A1    Feb. 2, 2023

(51) Int. Cl.
| | | |
|---|---|---|
| *G06T 11/00* | (2006.01) | |
| *A61B 6/02* | (2006.01) | |
| *A61B 6/50* | (2024.01) | |
| *G06T 7/62* | (2017.01) | |

(52) U.S. Cl.
CPC ............ *G06T 11/003* (2013.01); *A61B 6/025* (2013.01); *A61B 6/502* (2013.01); *G06T 7/62* (2017.01); *G06T 2207/10112* (2013.01); *G06T 2207/30068* (2013.01); *G06T 2207/30096* (2013.01)

(58) Field of Classification Search
None
See application file for complete search history.

(56) References Cited

U.S. PATENT DOCUMENTS

| | | | | |
|---|---|---|---|---|
| 7,992,100 | B2* | 8/2011 | Lundstrom | G16H 40/63 715/810 |
| 9,053,565 | B2* | 6/2015 | Buelow | G06T 19/00 |
| 9,613,440 | B2* | 4/2017 | Claus | A61B 6/025 |
| 10,111,631 | B2* | 10/2018 | Gkanatsios | A61B 6/5223 |
| 10,448,911 | B2* | 10/2019 | Erhard | A61B 6/4452 |
| 10,575,807 | B2 | 3/2020 | Gkanatsios et al. | |
| 10,786,218 | B2* | 9/2020 | Fukuyo | A61B 6/46 |
| 10,959,696 | B1* | 3/2021 | Douglas | G06T 7/62 |

(Continued)

FOREIGN PATENT DOCUMENTS

| | | | | |
|---|---|---|---|---|
| EP | 2779090 A1 * | 9/2014 | | A61B 6/502 |
| WO | 2011044295 A2 | 4/2011 | | |

OTHER PUBLICATIONS

EP patent application 22185815.2 filed Jul. 19, 2022—extended Search Report issued Oct. 13, 2022; 7 pages.

(Continued)

*Primary Examiner* — Randolph I Chu
(74) *Attorney, Agent, or Firm* — McCoy Russell LLP (57) ABSTRACT

Various systems are provided for non-uniform thickness and/or sampling of slabs of the breast to present DBT acquisitions. A method for generating a patient image as a set of slabs representing an imaged object, the method comprising acquiring a tomosynthesis projection, reconstructing a series of slab images, each slab representing a portion of a breast, and a plurality of slabs of non-uniform thickness and/or non-uniform sampling in a 3D reconstructed domain defined by x-, y-, and z-axes.

16 Claims, 6 Drawing Sheets

(56) References Cited

U.S. PATENT DOCUMENTS

| | | | | |
|---|---|---|---|---|
| 2004/0240605 A1* | 12/2004 | Tsujii | ............... | A61B 6/025 |
| | | | | 378/22 |
| 2006/0098855 A1* | 5/2006 | Gkanatsios | ............ | A61B 6/466 |
| | | | | 382/128 |
| 2007/0297659 A1 | 12/2007 | Collins | | |
| 2011/0028829 A1* | 2/2011 | Hu | ............... | A61B 5/055 |
| | | | | 600/413 |
| 2012/0195484 A1* | 8/2012 | Ren | ............... | G06F 18/22 |
| | | | | 382/131 |
| 2013/0022254 A1* | 1/2013 | Chen | ............... | G06T 7/149 |
| | | | | 382/128 |
| 2015/0036904 A1 | 2/2015 | Jerebko | | |
| 2015/0305705 A1* | 10/2015 | Goodenough | ......... | A61B 6/583 |
| | | | | 378/207 |
| 2017/0221201 A1* | 8/2017 | Chang | ............... | G06T 7/0012 |
| 2024/0020792 A1* | 1/2024 | Tohme | ............... | G06T 7/80 |

OTHER PUBLICATIONS

JP application 2022-111581 filed Jul. 12, 2022—Office Action issued Jul. 12, 2023; Machine Translation; 5 pages.

Van Schie, G. et al., "The Effect of Slab Size on Mass Detection Performance of a Screen-Film CAD System in Reconstructed Tomosynthesis Volumes," Proceedings of the International Workshop on Digital Mammography, Jun. 16, 2010, Girona, Catalonia, Spain, 8 pages.

* cited by examiner

METHODS AND SYSTEMS FOR BREAST TOMOSYNTHESIS

TECHNICAL FIELD

Embodiments of the subject matter disclosed herein relate to non-uniform sampling for digital breast tomosynthesis

DISCUSSION OF ART

X-ray tomosynthesis may be used as an alternative mammography technique that creates a 3D representation (e.g., a 3D model) of a breast. One mode for viewing a 3D model is by viewing a series of 2D images that form the 3D model, referred to as a stack. A 2D image within the stack may be referred to as a slice.

Some techniques for reviewing tomosynthesis images may include Computer Aided Detection (CAD). CAD may include a computer-based image analysis method that identifies suspected abnormalities, their location, and other characteristics. A CAD algorithm may target and mark areas of interest in the images.

BRIEF DESCRIPTION

In one embodiment, a method for generating a patient image as a set of slabs representing an imaged object, the method comprises acquiring a tomosynthesis projection, reconstructing a series of slab images, each slab representing a portion of a breast, and a plurality of slabs of non-uniform thickness and/or non-uniform sampling in a 3D reconstructed domain defined by x-, y-, and z-axes.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
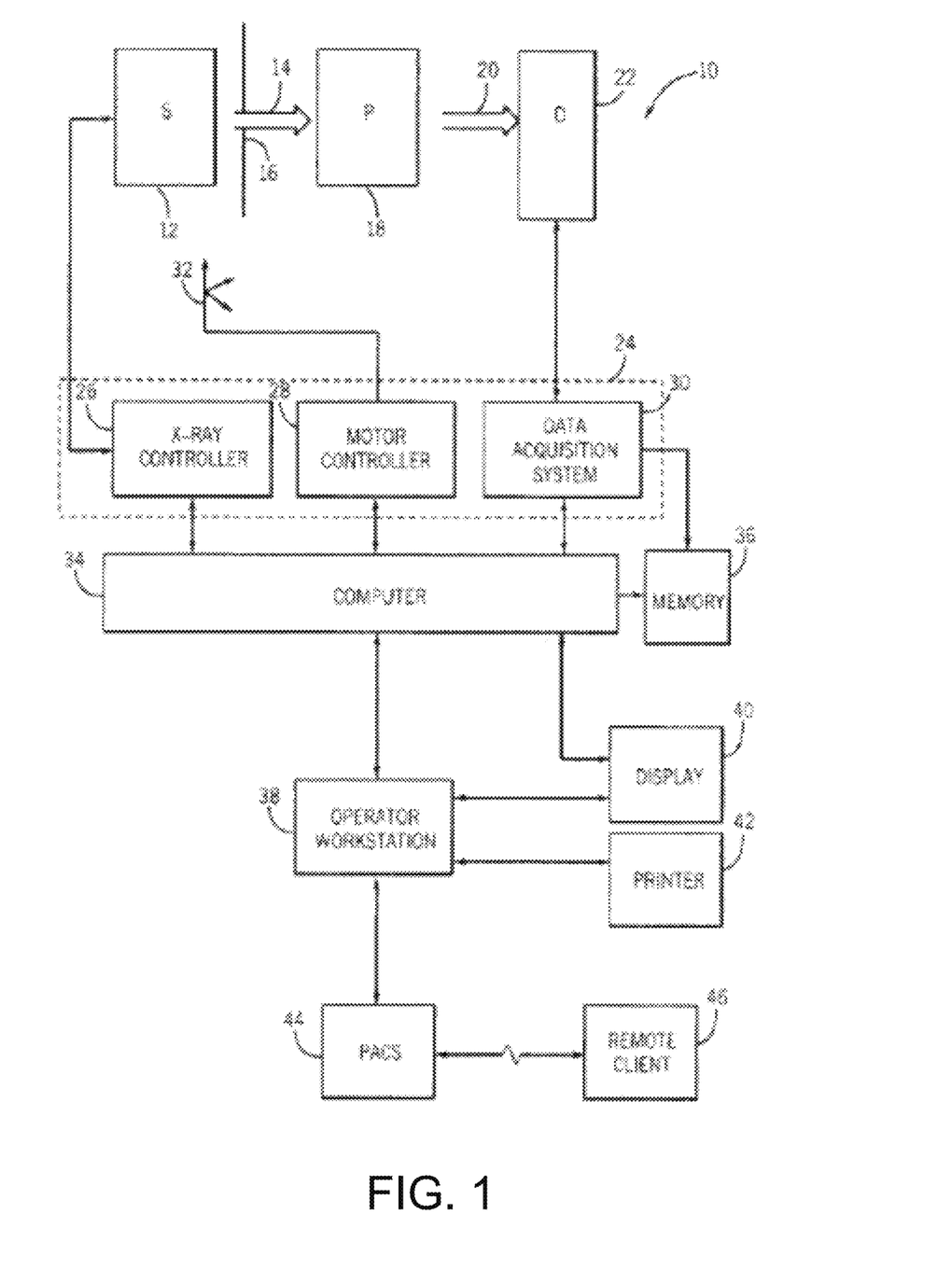
FIG. 1 shows a diagrammatical view of an exemplary imaging system.
Figure 2:
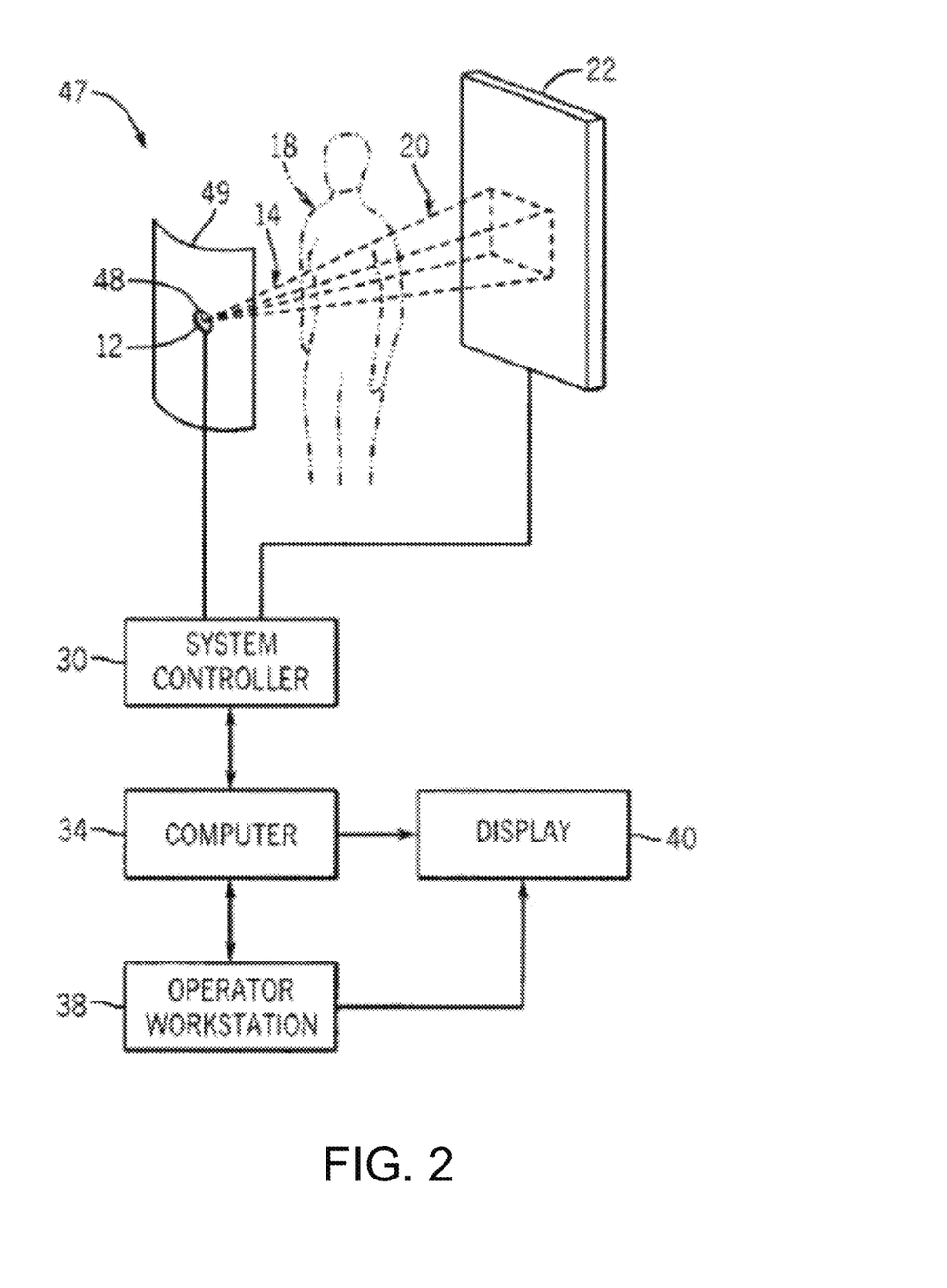
FIG. 2 shows a diagrammatical view of a real-world example of the exemplary imaging system.
Figure 3:
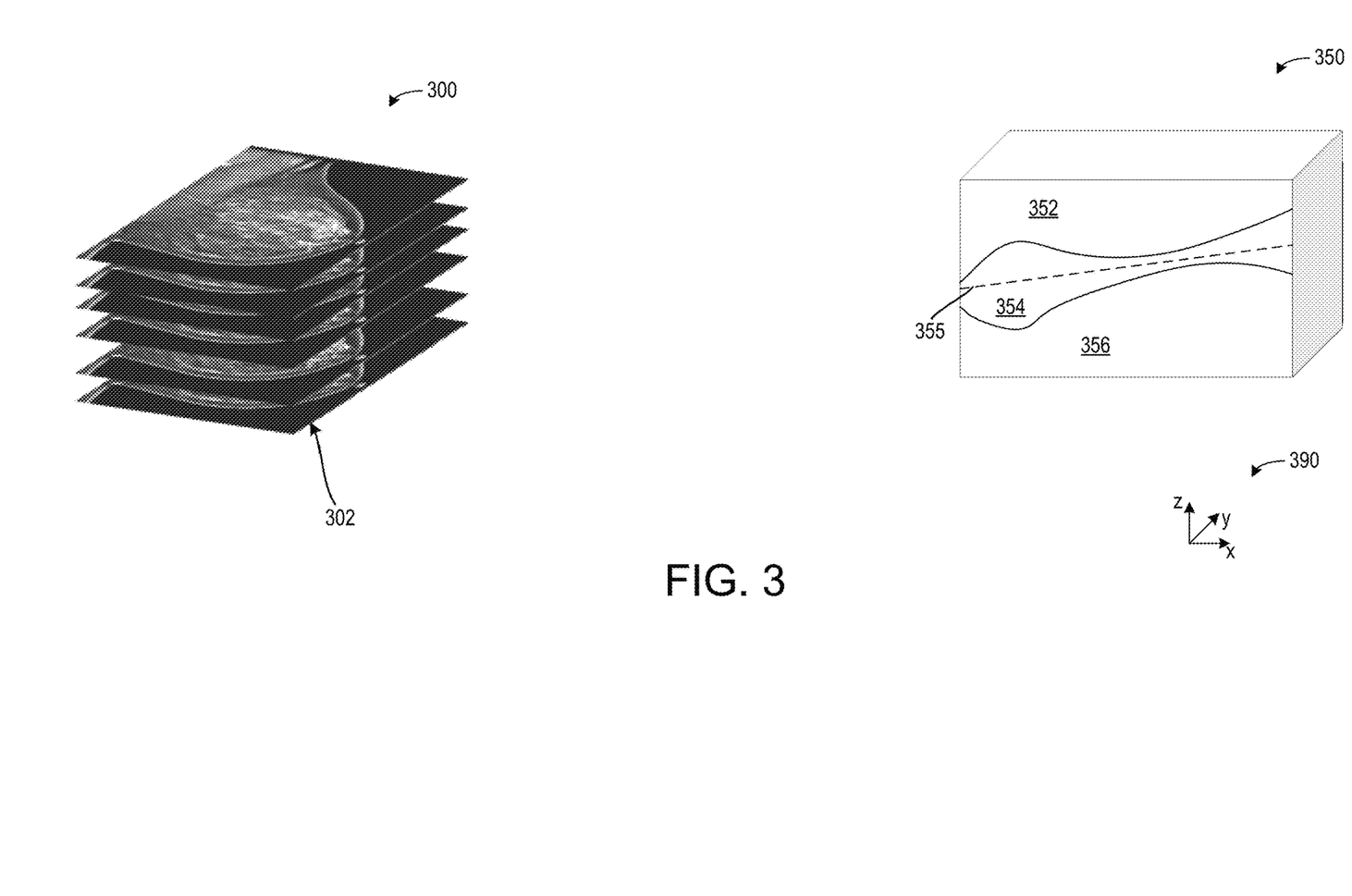
FIG. 3 shows a first example of generating non-uniform slabs of a digital breast tomography dataset.
Figure 4:
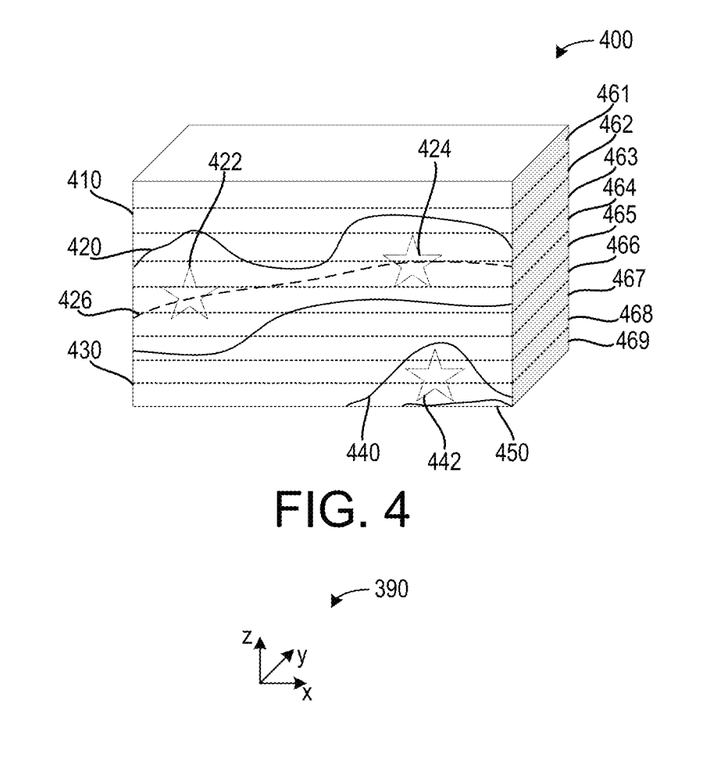
FIG. 4 shows a second example of generating non-uniform slabs of a digital breast tomography dataset.
Figure 5:
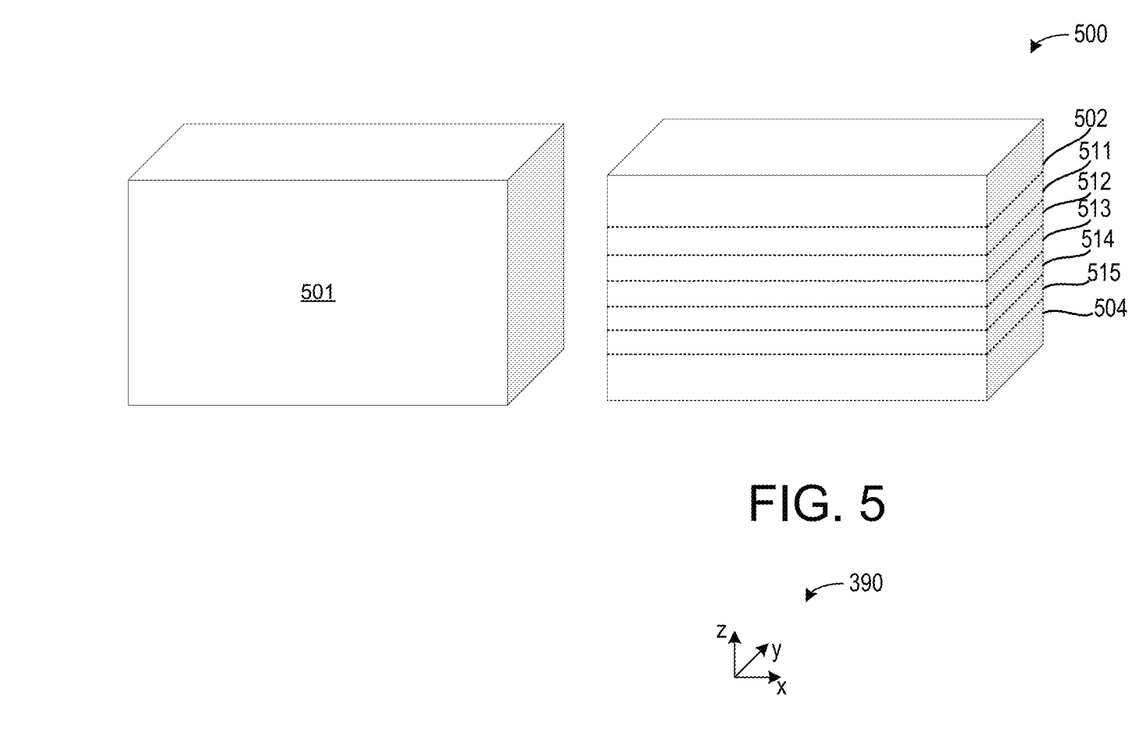
FIG. 5 shows a third example of generating non-uniform slabs of a digital breast tomography dataset.
Figure 6:
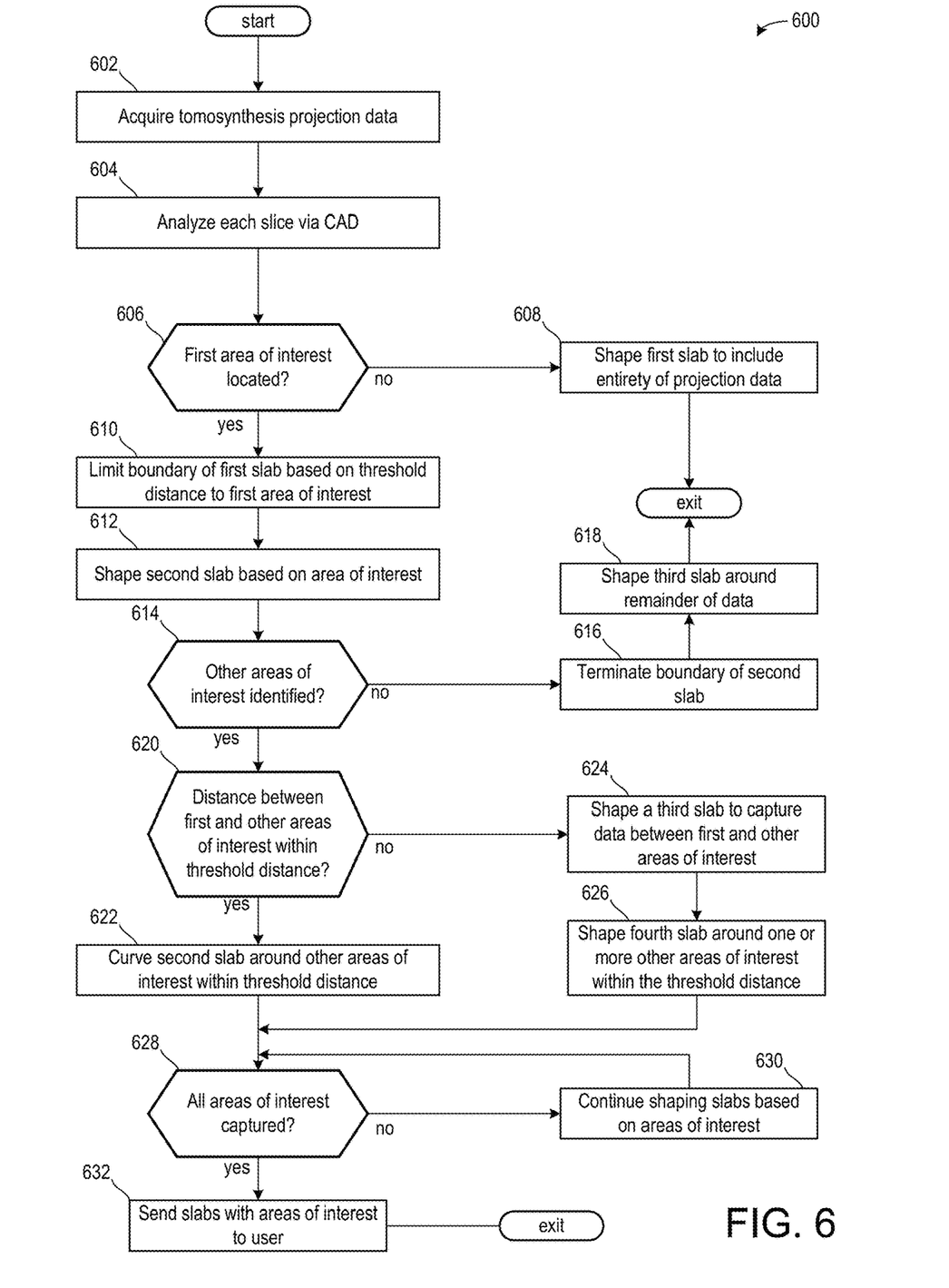
FIG. 6 shows a method for generating non-uniform slabs based on a digital breast tomography dataset.

The following description relates to embodiments of an imaging method to reconstruct a tomosynthesis image via non-uniform slabs. An example system for acquiring a digital breast tomography is illustrated in FIGS. 1 and 2. Examples for utilizing non-uniform slabs for generating an image of breast tissue scanned during a digital breast tomography (DBT) are shown in FIGS. 3, 4, and 5. A method for adjusting the shape of the slabs based on areas of interest in a volumetric image is shown in FIG. 6.

In one example, previous methods for reconstructing a DBT volume may include reconstructing extra planes at the top and bottom of the breast to account for uncertainties on the position of the top and bottom of the breast (due to breast support type, paddle type, spacer, compression force, etc.). These extra planes present may be of reduced image quality due to the presence of breast support or paddle and increase reading time and storage demands. In one embodiment according to the present disclosure, the first and last planes of a DBT volume may be replaced with non-uniform slabs, which may reduce memory use and improve image quality and reading times.

In an embodiment, a progressive transition with decreasing thickness slabs may be implemented to switch between slabs at the periphery to planes in the center of the breast. In another embodiment, a uniformity of the slabs may be adjusted, wherein slabs may be separated based on portions of the volumetric image including areas of interest and free of areas of interest. Areas of interest may include lesions, a tumor, a lump, a calcification, an abscess, or other deviation from tissue.

A lesion detector may be applied to the volumetric image, which may include a CAD or a manual annotation based on heuristics indicative of a lesion or of contrasted sharp features to drive the sampling and/or thickness of slabs. In an embodiment, a number of pre-determined parameters may drive this sampling. For example, a largest sampling step may include one sampling step or a number of samples per lesion. This may be set independently for each lesion type. Additionally or alternatively, parameters may be adjusted based on breast size, a previous scan history, and other patient factors.

An example method may include determining intervals along an axis normal to a scan plane where there are no identified areas of interest. If areas of interest continue to be unidentified due to their absence, each such interval is represented as one slab only. In this way, portions of the DBT image where no areas of interest are present may be grouped together in a single, non-uniform slab to minimize memory consumption and decrease reading times.

When there is a potential lesion or other form of area of interest, one embodiment of the present disclosure may include adapting the sampling to include a predetermined value or number of samples. For instance, parameters can be set for each mass, wherein a first area of interest may be included in a plurality of slabs and a second area of interest may be included in a single slab.

In another embodiment, additionally or alternatively, the local thickness of the slab is adapted resulting in a slab of variable thickness. It can be set either to show the central plane of the lesion, or encompass all of the lesion, or a desired outcome in between. For example, cross-sections of the lesion may be captured via two or more slabs.

If several potential lesions are in close vicinity of a z-axis (e.g., a vertical axis), then an embodiment may include slabs of uniform sampling in an x-y plane parallel to a detector and non-uniform in the z axis.

In another embodiment, a slab that is not parallel to the detector (either slanted plane or curved surface) of uniform thickness is curved relative to a 3D space (e.g., relative to each of an x-, a y-, and a z-axis).

In a further embodiment, a slab parallel to the detector may vary in thickness between different areas of interest at separate locations of the breast. In one example, the different areas of interest may be within a threshold distance of another or arranged along a common slice parallel to the x-y plane.

Due to the anisotropic nature of DBT, a threshold curvature for the slab may be set to avoid slicing volume too much in the vertical direction. The threshold curvature may be a non-zero, positive number based on one or more of a breast size, a number of slices being dissected, a previous scan history, and other imaging parameters.

FIGS. 1 to 2 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

FIG. 1 is a diagrammatical representation of an exemplary tomosynthesis system, designated generally by the reference numeral 10, for acquiring, processing and displaying tomosynthesis images, including images of various slices or slabs through a subject of interest in accordance with the present techniques. Slabs may depend on system parameters like breast support type, paddle type, spacer, compression force, and the like. In the embodiment illustrated in FIG. 1, the tomosynthesis system 10 includes a source 12 of X-ray radiation which is movable generally in a plane, or in three dimensions. In the exemplary embodiment, the X-ray source 12 typically includes an X-ray tube and associated support and filtering components. In one example, the support may correspond to an object on which a patient breast is positioned. Additionally or alternatively, the patient breast may be compressed between plates. The support and compression of the patient breast may define one or more imaging parameters.

A stream of radiation 14 is emitted by source 12 and passes into a region of a subject, such as a human patient 18. A collimator 16 serves to define the size and shape of the X-ray beam 14 that emerges from the X-ray source toward the subject. A portion of the radiation 20 passes through and around the subject, and impacts a detector array, represented generally by reference numeral 22. Detector elements of the array produce electrical signals that represent the intensity of the incident X-ray beam. These signals are acquired and processed to reconstruct an image of the features within the subject.

Source 12 is controlled by a system controller 24 which furnishes both power and control signals for tomosynthesis examination sequences, including position of the source 12 relative to the subject 18 and detector 22. Moreover, detector 22 is coupled to the system controller 24 which commands acquisition of the signals generated by the detector 22. The system controller 24 may also execute various signal processing and filtration functions, such as for initial adjustment of dynamic ranges, interleaving of digital image data, and so forth. The system controller 24 commands operation of the imaging system 10 to execute examination protocols and to process acquired data. In the present context, the system controller 24 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, the system controller 24 includes an X-ray controller 26 which regulates generation of X-rays by the source 12. In particular, the X-ray controller 26 is configured to provide power and timing signals to the X-ray source 12. A motor controller 28 serves to control movement of a positional subsystem 32 that regulates the position and orientation of the source 12 with respect to the subject 18 and detector 22. The positional subsystem may also cause movement of the detector 22, or even the patient 18, rather than or in addition to the source 12. It should be noted that in certain configurations, the positional subsystem 32 may be eliminated, particularly where multiple addressable sources 12 are provided. In such configurations, projections may be attained through the triggering of different sources of X-ray radiation positioned differentially relative to the patient 18 and/or source 22. Finally, in the illustration of FIG. 1, detector 22 is coupled to a data acquisition system 30 that receives data collected by read-out electronics of the detector 22. The data acquisition system 30 typically receives sampled analog signals from the detector and converts the signals to digital signals for subsequent processing by a computer 34. Such conversion, and indeed any preprocessing, may actually be performed to some degree within the detector assembly itself.

The computer 34 is typically coupled to the system controller 24. Data collected by the data acquisition system 30 is transmitted to the computer 34 and, moreover, to a memory device 36. Any suitable type of memory device, and indeed of a computer, may be adapted to the present techniques, particularly processors and memory devices adapted to process and store large amounts of data produced by the system 10. Moreover, the computer 34 may be configured to receive commands and scanning parameters from an operator via an operator workstation 38, typically equipped with a keyboard, mouse, or other input devices. An operator may control the system via these devices, and launch examinations for acquiring image data. Moreover, the computer 34 is adapted to perform reconstruction of the image data as discussed in greater detail below. Where desired, other computers or workstations may perform some or all of the functions of the present technique, including post-processing of image data accessed from memory device 36 or another memory device at the imaging system location or remote from that location.

In the diagrammatical illustration of FIG. 1, a display 40 is coupled to the operator workstation 38 for viewing reconstructed images and for controlling imaging. Additionally, the images may also be printed or otherwise output in a hardcopy form via a printer 42. The operator workstation, and the overall system may be coupled to large image data storage devices, such as a Picture Archiving and Communication System ("PACS") 44. The PACS 44 may be coupled to a remote client, as illustrated at reference numeral 46, such as for requesting and transmitting images and image data for remote viewing and processing as described herein. It should be further noted that the computer 34 and operator workstation 38 may be coupled to other output devices which may include standard or special-purpose computer monitors, computers and associated processing circuitry. One or more operator workstations 38 may be further linked in the system for outputting system parameters, requesting examinations, viewing images, and so forth. In general, displays, printers, workstations and similar devices supplied within the system may be local to the data acquisition components or remote from these components, such as elsewhere within an institution or in an entirely different location, being linked to the imaging system by any suitable network, such as the Internet, virtual private networks, local area networks, and so forth.

Referring generally to FIG. 2, an exemplary implementation of a tomosynthesis imaging system of the type discussed with respect to FIG. 1 is illustrated. Although a particular tomosynthesis imaging system is illustrated in FIG. 2, note that any other type of tomosynthesis image system, such as one associated with mammograms, may be used in accordance with any of the embodiments described herein. As shown in FIG. 2, an imaging scanner 47 generally permits interposition of a subject 18 between the source 12 and detector 22. Although a space is shown between the subject and detector 22 in FIG. 2, in some embodiments, the subject may be positioned directly before or against the imaging plane of the detector 22. For example, in digital breast tomosynthesis (DBT) the imaged breast is generally positioned directly above the detector cover. The detector 22 may, moreover, vary in size and configuration. The X-ray source 12 is illustrated as being positioned at a source location or position 48 for generating one or a series of projections. In general, the source is movable relative to the imaged anatomy such as to permit multiple such projections to be attained in an imaging sequence. In the illustration of FIG. 2, a curved source surface 49 is defined by the array of positions available to source 12. This curved source surface 49 may be representative of, for example, an X-ray tube attached to a gantry arm which rotates around a pivot point in order to acquire projections from different views. The source surface 49 may be replaced by other three-dimensional trajectories for a movable source 12. Alternatively, two-dimensional or three-dimensional layouts and configurations may be defined for multiple sources which may or may not be independently movable.

In typical operation, X-ray source 12 projects an X-ray beam from its focal point toward detector 22. A portion of the beam 14 that traverses the subject 18, results in attenuated X-rays 20 which impact detector 22. This radiation is thus attenuated or absorbed by the internal features of the subject, such as internal anatomies in the case of medical imaging. The detector 22 is formed by a plurality of detector elements generally corresponding to discrete picture elements or pixels in the resulting image data. The individual pixel electronics detect the intensity of the radiation impacting each pixel location and produce output signals representative of the radiation. In an exemplary embodiment, the detector consists of an array of 2048×2048 pixels. In another embodiment, the detector consists of an array of 2304×1920 pixels. Other detector configurations and resolutions are, of course, possible. Each detector element at each pixel location produces an analog signal representative of the impending radiation that is converted to a digital value for processing.

The source 12 is moved and triggered, or offset distributed sources are similarly triggered, to produce a plurality of projections or images from different source locations. These projections are produced at different view angles and the resulting data (i.e., the projection radiographs) is collected by the imaging system. In an exemplary embodiment involving breast imaging, the gantry or arm to which the source 12 is attached has a pivot point located at the same height as the detector 22. The distance from the focal point of the source 12 to the pivot point of the gantry or arm is 66.0 cm or another distance. The considered angular range of the gantry with respect to the pivot point is from −30 to 30 degrees, where 0 degrees corresponds to the vertical position of the gantry arm (i.e., the position where the center ray of the X-ray cone beam is perpendicular to the detector plane). With this system, typically 21 projection radiographs are acquired, each 3 degrees apart covering the full angular range of the gantry, although the number of images and their angular separation may vary. This set of projection radiographs constitutes the tomosynthesis projection dataset.

Embodiments of the present disclosure may include a method for generating a patient image representing an imaged object. The method may include acquiring tomosynthesis projection data. The tomosynthesis projection data may be analyzed and divided into a plurality of slices. The plurality of slices may be constructed based on projections of the tomosynthesis projection data via a reconstruction algorithm. In one example, each of the plurality of slices is arranged in an x-y plane and separated along a z-axis normal to the x-y plane. A computer assisted detection may identify one or more areas of interest and generate the patient image with one or more slabs via a controller based on the acquired tomosynthesis projection data, wherein the one or more slabs include data from all or a portion of one or more of the plurality of slices.

The one or more slabs may be non-uniform about one or more of an x-, a y-, or the z-axis based on locations of the areas of interest. For example, shaping a first slab type may be based on portions of the plurality of slices free of areas of interest. The shaping may be determined based on thickness and/or sampling parameters. Alternatively, shaping a second slab type of the one or more slabs may be based on portions of the plurality of slices comprising areas of interest. Shaping the first slab type and the second slab type may be based on a threshold distance to an area of interest, wherein shaping the first slab type comprises shaping the first slab type at least the threshold distance away from the area of interest and shaping the second slab type comprising shaping the second slab type within the threshold distance of the area of interest. Shaping the second slab type to comprise a first area of interest and a second area of interest may include curving, slanting, angling, or adjusting dimensions of boundaries of the second slab type relative to the x-, y-, and z-axis. A size of the second slab type may be reduced such that excess data distal to the area of interest is not included. A size of the first slab type may be maximized such that a remainder of the plurality of slices is represented in as few slabs as possible.

In one example, the first slab type and the second slab type may be non-uniform. The first slab type may be non-uniform and angled about one or more of the x-, the y-, and the z-axes, wherein the non-uniform first slab type includes portions of the plurality of slices free of areas of interest. The second slab type may be non-uniform and angled about one or more of the x-, the y-, and the z-axes, wherein the non-uniform second slab type includes portion of the plurality of slices including the areas of interest. A patient image may include plurality of the first slab type and the second slab type, wherein each of the first and second slab types may be different from one another (e.g., non-uniform). In this way, each second slab type may be tailored to a size and shape of each area of interest and each first slab type may be tailored to be free of the areas of interest. In some examples, the first slab type and the second slab type may be optionally curved.

In some examples, the threshold distance may be a fixed value, uniform about each of the x-, y-, and z-axes. In this way, for a DBT with a single area of interest, a shape of a slab including portions of slices including the single area of interest may be substantially spherical in shape. Additionally or alternatively, the threshold distance may be a dynamic value adjusted based on one or more scan settings and patient factors. For example, the threshold distance may be smaller along the z-axis and larger along the x- and y-axes. Additionally or alternatively, the threshold distance may decrease as a size of a slab increases. That is to say, the threshold distance may be a first value at an initial generation of a slab, and then reduced to a second value less than the first value as a size of the slab is increased. Additionally or alternatively, in some embodiment, the threshold distance may be adjusted based on a type of area of interest. The threshold distance may be measured from a centroid of an area of interest or from an outer perimeter of the area of interest.

In another embodiment, a system for an imaging device comprises a detector operated via a controller. The controller may include instructions stored on non-transitory memory thereof that when executed cause the controller to acquire tomosynthesis projection data and generator a plurality of slices based on projections of the tomosynthesis projection data. Each of the plurality of slices may be separated along a z-axis normal to the x-y plane. A computer aided detection (CAD) is configured to electronically analyze and identify areas of interest in the plurality of slices. The CAD may shape a plurality of first slab types configured to capture data in the plurality of slices a threshold distance away from each of the areas of interest. The CAD may shape a plurality of second slab types configured to capture data in the plurality of slices within the threshold distance of each of the areas of interest, the threshold distance measured along a three-dimensional axis system including an x-axis, a y-axis, and the z-axis. The plurality of first and second slab types are curved. A size of the plurality of first slab types in response to areas of interest not being identified may be maximized. A size of the plurality of second slab types may be minimized. The plurality of second slab types include data from only portions of the plurality of slices within the threshold distance of the areas of interest. Remaining portions of the plurality of slices are included in the plurality of first slab types. The CAD may shape a first slab type of the plurality of first slab types to include a portion of a first slice of the plurality of slices free of an area of interest, and wherein the instructions cause the controller to shape a second slab type to include a remaining portion of the first slice of the plurality of slices comprising the area of interest. The plurality of first slab types and the plurality of second slab types may be shaped non-parallel to the detector. The plurality of first slab types and the plurality of second slab types may be angled to the x-y plane. A single slab of the plurality of second slab types includes two or more of the areas of interest in response to the two or more areas of interest being within the threshold distance of each other. One of the plurality of second slab types includes a first area of interest and another of the plurality of second slab types includes a second area of interest. A distance between the first area of interest and the second area of interest is greater than the threshold distance.

Additionally or alternatively, data from a slice comprising an area of interest may be divided into a first slab and a second slab, wherein the first slab comprises data from a subset of the slice a threshold distance away from the area of interest, and the second slab comprises data from a different subset of the slice within the threshold distance of the area of interest. The threshold distance may be adjustable based on a breast thickness. Each of the areas of interest are arranged in one of the plurality of slabs. Different slabs of the plurality of slabs comprising different areas of interest are separated by slabs free of areas of interest.

Turning now to FIG. 3, it shows an example of a DBT 300 along with a volumetric image 350 illustrated via a plurality of slabs based on slices of the DBT 300. The DBT 300 may be of a left or a right breast of a patient, such as subject 18 of FIG. 1. The DBT 300 may include a plurality of slices 302, each slice may be acquired parallel to an x-y plane with reference to axis system 390. The x-y plane is parallel to a plane of detection of a detector, in one example. Each of the plurality of slices 302 may be separated along a z-axis normal to the x-y plane.

The volumetric image 350 may include three slabs, including a first slab 352, a second slab 354, and a third slab 356. The dimensions of each of the first slab 352, the second slab 354, and the third slab 356 may be adjusted based on identified areas of interest within the plurality of slices 302. For example, the first slab 352 and the third slab 356 may be a first slab type and free of any detected areas of interest. In one example, a computer assisted detection (CAD) may detect areas of interest, wherein locations free of areas of interest may be combined in the each of the x-, y-, and z-axes.

In one example, a slab is generated via merging of two or more slices of the plurality of slices 302. Each slice, which corresponds to a detection of x-ray intensity by the detector, may be reconstructed into an image. Thus, a slab may include merging images together by averaging or applying a maximum intensity projection or any other merging method. Thus, a slab may provide more data into a single image, which allows more concise imaging to be provided to a medical professional. In an example of the present disclosure, the slabs generated may include more pertinent information in one type of slab, such as sections of DBT via abnormal detections (e.g., areas of interest) with less normal sections (e.g. sections free of areas of interest).

The second slab 354 may be a second slab type and include one or more areas of interest within a threshold distance of one another. In one example, the threshold distance is based on a non-zero, positive number and is measured along the z-axis. The second slab 354 may include sections of multiple slices of the plurality of slices 302 separated along the z-axis. The second slab may include a variable thickness within the slab that is not parallel to the detector. That is to say, the variable thickness may be varied along the z-axis. Additionally or alternatively, the boundaries of the second slab 354 may be adjusted in the x- and y-axes, respectively. A central axis 355 of the second slab 354 is included, wherein a shape of the second slab 354 may be partially defined by the central axis 355. An entirety of the central axis 355 is included in the second slab 354. In one example, a shape of the second slab 354 may be at least partially defined by the central axis 355.

A local thickness of the second slab 354 may vary at different locations along the x-y plane. For example, the second slab 354 may be thicker in some regions and thinner in other regions based on a portion of a breast, an area of interest, or imaging parameters.

In one example, a user, such as a physician or other medical professional, may analyze only the second slab 354. As such, the image acquisition and presentation of FIG. 3 may use less memory and improve review times relative to other tomography methodologies.

Thus, in the example of FIG. 3, a plurality of slabs may be shaped based on locations of areas of interest. The slabs may be divided into first slab types and second slab types. The first slab types, which may include the first slab 352 and the third slab 356, are free of areas of interest and the second slab types may include the second slab 354 and includes areas of interest. The first slab types and the second slab types may be complementary to one another. That is to say, curves of first slab types and the second slab types are complementary.

Turning to FIG. 4, it shows a second example 400 of multiple variable thickness slabs for representing a plurality of slices of a volumetric image of a DBT. The second example 400 may include a first slab 410, a second slab 420, a third slab 430, a fourth slab 440, and a fifth slab 450. The first slab 410, the third slab 430, and the fifth slab 450 are free of areas of interest and may be a first slab type.

The second slab 420 may include a first area of interest 422 and a second area of interest 424. A central axis 426 of the second slab 420 may extend through each of the first area of interest 422 and the second area of interest 424. The second slab 420 may curve along each of the x-, y-, and z-axes based on each of a location of the first area of interest 422 and the second area of interest 424. In one example, curving of the second slab 420 is used to tailor a size of the second slab 420 to be within the threshold distance of the first area of interest 422 and the second area of interest 424. Additionally or alternatively, a size of the second slab 420 may be reduced at a location between the first area of interest 422 and the second area of interest 424. In one example, the second slab 420 may include data from a plurality of slices, wherein the data included from the plurality of slices is within the threshold distance of at least one of the first area of interest 422 and the second area of interest 424. As such, the second slab 420 may include only portions of slices, wherein other portions of the slices may be included in the first slab 410, the third slab 430, the fourth slab 440, and/or the fifth slab 450.

The fourth slab 440 may include a third area of interest 442. The fourth slab 440 may be separated from the second slab 420 due to a distance between the third area of interest 442 and the second area of interest 424 or the first area of interest 422 being greater than the threshold distance.

In the example of FIG. 4, areas of interest are included in only a single slab. However, during some image acquisitions, an area of interest may be included in multiple slabs such that the slabs overlap. Additionally or alternatively, some slabs may include only a centerline or other landmark feature of an area of interest.

The plurality of slices may include a first slice 461, a second slice 462, a third slice 463, a fourth slice 464, a fifth slice 465, a sixth slice 466, a seventh slice 467, an eighth slice 468, and a ninth slice 469. Each slice may be generated based on a scan of an object, such as a breast. Dimensions of each slice of the plurality of slices may be fixed, wherein each slice is parallel to the x-y plane.

The first slab 410 may include portions of the first slice 461, the second slice 462, the third slice 463, and the fourth slice 464. The second slab 420 may include data from the second slice 462, the third slice 463, the fourth slice 464, the fifth slice 465, the sixth slice 466, and the seventh slice 467. The third slab 430 may include portions of the fifth slice 465, the sixth slice 466, the seventh slice 467, the eighth slice 468, and the ninth slice 469. The fourth slab 440 may include portions of the seventh slice 467, the eighth slice 468, and the ninth slice 469. The fifth slab 450 may include portions of only the ninth slice 469.

In some examples, additionally or alternatively, the slabs shaped may not extend fully across the x-y plane of a slice of the plurality of slices. An extension of the slabs along the z-axis may be shaped such that a single slab may include a height along the z-axis less than a total height of all the slices stacked together.

In this way, data from each of the plurality of slices may be divided into different slabs based on detected areas of interest. The first area of interest 422 may be included in the fourth slice 464, the fifth slice 465, and the sixth slice 466. The second area of interest 424 may be included in the third slice 463 and the fourth slice 464. The third area of interest 442 may be included in the seventh slice 467, the eighth slice 468, and the ninth slice 469. The second and fourth slabs may be shaped and curved to minimize inclusion of data not associated with the areas of interest. For example, a size of the first slab 420 may not extend to within the threshold distance along one or more of the x-, y-, and z-axes of the first and second areas of interest 422, 424. In some examples, the threshold distance may be adjusted if two or more areas of interest are included within a single slice. For example, a distance along the x-axis between the first area of interest 422 and the second area of interest 424 may be greater than the threshold distance. However, since each of the first area of interest 422 and the second area of interest 424 are included in the fourth slice 464, then a corresponding slab (e.g., the second slab 420) may be shaped to include both.

A medical professional may receive only the second slab 420 and the fourth slab 440, which may represent a 3D image of the object. Each slab may be a 2D representation of a different 3D image. The sections of the slices not included in the second slab 420 and the fourth slab 440 may not be included, which may reduce a read time of the medical professional.

In some examples, the slabs may be shaped to include each of the areas of interest as a whole unit. In this way, an area of interest may not be divided with different portions included in different slabs. In some examples, additionally or alternatively, the area of interest may be divided and different portions thereof may be included in different adjacent slabs. In some embodiments, additionally or alternatively, the slabs may overlap and include identical portions of the area of interest, which may allow a medical professional to analyze different views of the area of interest.

In this way, FIGS. 3 and 4 illustrate examples of generating non-uniform slabs for representing areas of interest. The slabs may include different portions of a plurality of slices, wherein data from each slice of the plurality of slices may be included in one or more slabs. A shape of each of the slabs may be adjusted along each of the x-, y-, and z-axes to tailor the slab to include only data adjacent to areas of interest or to maximize a slab size including data not related to areas of interest.

Turning now to FIG. 5, it shows a third example 500 of multiple variable thickness slabs for representing a plurality of slices of a volumetric image of a DBT 501. In the third example 500, the DBT 501 is divided into periphery slabs and interior slabs. The periphery slabs may include a first periphery slab 502 and a second periphery slab 504. The first periphery slab 502 and the second periphery slab 504 may define extreme ends of the DBT, corresponding to a top and a bottom of a patient breast along the z-axis. In one example, the top and the bottom of the patient breast may be free of areas of interest. That is to say, it may be unlikely to scan areas of interest, such as a lesion, in the top or the bottom of the patient breast. As such, a thickness of the first periphery slab 502 and the second periphery slab 504 may be greater than a thickness of interior slabs such that the slabs are non-uniform.

The interior slabs may include a first interior slab 511, a second interior slab 512, a third interior slab 513, a fourth interior slab 514, and a fifth interior slab 515. In the example of FIG. 5 the interior slabs may be include a thickness uniform to one another and less thick than the periphery slabs. This may reduce processing times. Additionally or alternatively, a thickness of the interior slabs may be non-uniform based on locations, types, and occurrences of areas of interest. In this way, the slab thicknesses may be based on a height of a portion of a breast. For example, if the portion of the breast is an extreme end of the breast along the z-axis, then the slab thickness may be increased and the sampling may be more coarse. If the portion of the breast is between the extreme ends, then the slab thickness may be reduced and the sampling may be more fine.

In one example, the thickness and/or a sampling of the DBT may be non-uniform. A slab thickness and/or sampling may be based on imaging system parameters including a thickness of the breast, an average lesion size, a tomosynthesis aperture angle and/or a paddle type. The aperture angle may correspond to an acquisition tomosynthesis system aperture. For example, the thickness of the slabs may be relatively small and the sampling may be relatively fine. As another example, the thickness of the slabs may be relatively large and the sampling may be relatively coarse. In such an example, an overlap of the slabs may increase. Additionally or alternatively, thickness and sampling may be adjusted depending on a location of the patient breast. In the example of FIG. 5, the thickness is increased and the sampling is more coarse at the periphery of the breast. This may be due artifacts appearing the imaging, reducing a quality thereof. Additionally or alternatively, the thickness and/or sampling may be adjusted in response to an area of interest. For example, the thickness may decrease and/or the sampling may become more fine for slabs including an area of interest. A number of slabs may increase when the sampling is more fine. Thus, in the absence of an area of interest, the thickness may increase and the sampling may be more coarse.

In some examples, the thickness, which may be measured normal or at an angle (e.g., between 0 and 180 degrees) to the x-y plane, may be non-uniform. That is to say, thickness of the slabs may be non-uniform to one another and along body of a single slab. As such, the single slab may include multiple thicknesses. The single slab may be customized via curves, slants, or other deviations from parallel to the 3D axis system.

In some examples, the slab sampling may be non-uniform. For example, more slabs may include an area of interest (e.g., a finer slab sampling) and fewer slabs may include locations free of areas of interest (e.g., coarser slab sampling). Furthermore, a magnitude of the fine sampling may be adjusted based on the area of interest. For example, a smaller area of interest may include finer sampling than a larger area of interest, which may include less fine sampling. Additionally or alternatively, if the area of interest is new and was not present in a previous patient imaging, then the sampling may be finer relative to sampling of an area of interest included in previous patient images.

In one example, a slab thickness and/or sampling is based on imaging system parameters including a thickness of the breast, an average lesion size, a tomosynthesis aperture angle and/or a paddle type. For example, as the thickness of the breast decreases, the thickness of the slab may decrease and/or the sampling may become more fine. As another example, as the average lesion size increases, the slab thickness may increase and/or the sampling may become more coarse. As the aperture angle decreases, the slab thickness may increase and/or the sampling may become more coarse. A method for adjusting slab sizes based on areas of interest, including a size of the area of interest, is shown in FIG. 6.

Turning not to FIG. 6, it shows a method 600 for shaping a plurality of slabs based on areas of interest located in a plurality of slices of a DBT scan. Instructions for carrying out method 600 may be executed by a controller or a computer based on instructions stored on a memory of the controller and in conjunction with signals received from sensors of the imaging system, such as the sensors described above with reference to FIGS. 1 and 2. The controller may shape one or more slabs based on data gathered via CAD.

The method 600 begins at 602, which includes acquiring tomosynthesis projection data. The projection data may be, for example, associated with a digital breast tomosynthesis system and may be acquired in substantially real time or comprise stored data that was previously acquired. The data may be gathered as a plurality of slices, each slice extending in a direction substantially parallel to a detector. In one example, the projection data is reconstructed into a plurality of slices (e.g., 2D images) prior to executing a CAD.

At 604, the method 600 may include analyzing each slice via the CAD. The CAD may identify a border and/or a centroid of one or more areas of interest include in the plurality of slices. The CAD may determine a threshold distance from the border and/or the centroid in each of an x-, y-, and z-axes, which may be used to determine slab shapes, as will be described herein.

At 606, the method 600 may include determining if a first area of interest is located. In one example, the first area of interest may include a tumor, a lump, a calcification, an abscess, or other deviation from tissue or clinically-relevant anatomical feature.

If no areas of interest are found, then at 608, the method 600 may include shaping a first slab to include an entirety of the projection data in the plurality of slices. As such, the first slab, which is the only slab, may be the only 2D image representing a 3D object (e.g., a breast) shaped via the CAD. As described above, a slab, such as the first slab, may include averaging or applying a maximum intensity projection of the slices included therein or any other slice aggregation method.

If a first area of interest is located, then at 610, the method 600 may include limiting a boundary of the first slab based on a threshold distance to the first area of interest. Limiting the boundary of the first slab may include shaping the first slab via the CAD away from the first area of interest at an amount equal to the threshold distance. Shaping the slab may include contouring, curving, angling, and zig-zagging boundaries of the first slab, wherein areas within the boundaries correspond to data to be included from the plurality of slices. For areas of the plurality of slices away from the first area of interest by greater than the threshold distance, the boundaries of the first slab may be continued. In this way, the first slab may be curved and include all of and/or portions of the plurality of slices.

At 612, the method 600 may include shaping the second slab based on the first area of interest. Borders of the second slab may be spaced away from the first area of interest by a distance equal to or less than the threshold distance. As described above, the threshold distance may be measured along any of the x-, y-, or z-axes. In one example, the threshold distance may be measured along only the z-axis, wherein the z-axis corresponds to an axis about which each of the plurality of slices is separated. By curving the second slab along each of the x-, y-, and z-axes about the first area of interest, a size of the second slab may be reduced due to the second slab only containing portions of slices within the threshold distance of the first area of interest. In this way, the second slab may illustrate the first area of interest while consuming less memory relative to other examples which may include entire slices that include data with regard to an area of interest.

At 614, the method 600 may include determining if other areas of interest are identified. Other areas of interest may be located on slices identical to the first area of interest or on one or more different slices.

If other areas of interest are not identified, then at 616, the method 600 may include terminating boundaries of the second slab. The boundaries may be terminated to be within the threshold distance of the first area of interest. As such, a size of the second slab is optimized to focus on only the first area of interest.

At 618, the method 600 may include shaping a third slab around a remainder of the data. In some examples, additionally or alternatively, the first slab may be extended such that the plurality of slices is illustrated entirely by only the first slab and the second slab.

Returning to 614, if other areas of interest are identified, then at 620, the method 600 may include determining if the first area of interest and other areas of interest are within the threshold distance to one another. If the first area of interest and other areas of interest are within the threshold distance of one another, then at 622, the method 600 may include curving the second slab around the other areas of interest within the threshold distance of the first area of interest. As such, the second slab may be extended along the x-, y-, and z-axes toward the other areas of interest. In some examples, dimensions of the second slab may be reduced at areas between areas of interest. As such, the second slab may narrow and then expand upon approaching different areas of interest. This may further reduce memory consumption and analyzing times.

If the other areas or interest are not within the threshold distance to the first area of interest, then at 624, the method 600 may include shaping a third slab to capture data between the first and other areas of interest.

At 626, the method 600 may include shaping a fourth slab around one or more other areas of interest within the threshold distance of one another. The fourth slab may be separated from the second slab. In one example, the fourth slab does not touch the second slab, wherein overlap between the fourth and second slab does not occur. In one example, the third slab may be directly between the second slab and the fourth slab. In some examples, additionally or alternatively, the fourth slab and the second slab may include data from different portions of identical slices. More specifically, a slice may be represented by each of the second, third, and fourth slabs based on a positioning of the areas of interest. In this way, only relevant portions of a slice may be included in one or more slabs to be interpreted by a user.

Following 622 and 626, at 628, the method 600 may include determining if all areas of interest are captured via a slab. If all areas of interest are not captured, then at 630, the method 600 may include continuing to curve slabs based on locations of the areas of interest. A plurality of slabs may be generated, the plurality of slabs including a first slab type which may include portions of the slices that are free of areas of interest and a second slab type which may include portions of the slices that include areas of interest. A size of the first slab type may be maximized and a size of the second slab type may be minimized.

If all areas of interest are captured with a slab, then at 632, the method 600 may include sending slabs with areas of interest (e.g., the second slab type) to a user. Slabs without areas of interest may be stored in memory, such as the PACS. In one example, slabs without areas of interest may be deleted. In one example, a display device may display images of only the slabs including areas of interest from the plurality of slices. In some examples, all slabs generated may be displayed to the user, wherein the display may include the categorizing the slabs as abnormal and normal. Abnormal slabs include the areas of interest and normal slabs are free of the areas of interest.

In some examples of the method, additionally or alternatively, the CAD may determine a number of lesions in the plurality of slices. A distance between each of the lesions may be calculated to determine if they are within the threshold distance. In examples wherein a largest slab size is defined, then sampling of the plurality of slices may include where slabs of uniform thickness are sampled. Neighboring slabs may overlap with one another such that neighboring slabs are half overlapping with one another. Each slab may intersect at locations with or without areas of interest.

If an area of interest is present, if a number of overlapping slabs is greater than a threshold number, then the slabs may be combined. If the number of overlapping slabs is less than the threshold number, then a slab that overlaps the most with the area of interest may be selected. Additionally or alternatively, a slab that overlaps with a greatest portion of a central axis of the area of interest may be selected. Other portions of the area of interest may be represented via neighboring slabs.

Additionally or alternatively, the slab may be curved or angled relative to a plane of the detector (e.g., angled to a slice of the plurality of slices). If the slab is being curved around two or more areas of interest, then a magnitude of the curvature may be limited based on the plane of the detector. For example, if the slab is curved beyond a threshold curvature, then multiple slabs may be used more parallel to the plane of the detector (e.g., less curved). Additionally or alternatively, each slab may be shaped to include only a single area of interest to reduce an amount of curving.

An example of a method for generating a patient image representing an imaged object, comprises acquiring tomosynthesis projection data via a plurality of slices each gathered in a respective x-y plane and separated along a z-axis normal to each x-y plane and generating the patient image with a slab via a processor based on the acquired tomosynthesis projection data, wherein the patient image is one of a plurality of patient images, wherein the one or more slabs include data from all or a portion of one or more of the plurality of slices, each of the slabs corresponding to different patient images of the plurality of patient images, and wherein the patient image is generated from a single, non-uniform slab including data from only a portion of a slice of the plurality of slices. A first example of the method further includes where the one or more slabs is curved about one or more of an x-, a y-, or the z-axis. A second example of the method, optionally including the first example, further includes where shaping a first slab type of the one or more slabs to include portions of the plurality of slices free of areas of interest. A third example of the method, optionally including one or more of the previous examples, further includes where shaping a second slab type of the one or more slabs to include portions of the plurality of slices comprising areas of interest. A fourth example of the method, optionally including one or more of the previous examples, further includes where shaping the first slab type and the second slab type is based on a threshold distance to an area of interest, wherein shaping the first slab type comprises shaping the first slab type at least the threshold distance away from the area of interest and shaping the second slab type comprising shaping the second slab type within the threshold distance of the area of interest. A fifth example of the method, optionally including one or more of the previous examples, further includes where shaping the second slab type to comprise a first area of interest and a second area of interest, wherein the shaping further comprises decreasing a size of the second slab type at a location between the first area of interest and the second area of interest. A sixth example of the method, optionally including one or more of the previous examples, further includes where maximizing a size of the first slab type and minimizing a size of the second slab type.

As used herein, an element or step recited in the singular and proceeded with the word "a" or "an" should be understood as not excluding plural of said elements or steps, unless such exclusion is explicitly stated. Furthermore, references to "one embodiment" of the invention do not exclude the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   acquiring a tomosynthesis projection volume of a breast; and
   reconstructing a series of slab images from the tomosynthesis projection volume;
   wherein the series of slab images is formed from a plurality of slabs of the tomosynthesis projection volume, wherein at least some of the plurality of slabs are of non-uniform thickness and/or non-uniform sampling in a 3D reconstructed domain defined by x-, y-, and z-axes, wherein two or more slabs of the plurality of slabs are curved, and wherein curves of the two or more slabs are complementary to one another.

2. The method of claim 1, wherein a slab thickness and/or sampling of at least one slab is based on imaging system parameters including a thickness of the breast, an average lesion size, a tomosynthesis aperture angle, and/or a paddle type.

3. The method of claim 1, wherein a slab thickness and/or sampling of at least one slab is based on an area of interest, and wherein a detection algorithm determines areas of interest in the breast.

4. The method of claim 1, wherein at least one slab is parallel to an x-y plane with a variable local thickness in relation to the x-y plane.

5. The method of claim 4, wherein a local thickness of the at least one slab is determined based on a location of an area of interest in the breast.

6. The method of claim 5, wherein the local thickness of the at least one slab is tailored to include the area of interest and reduce inclusion of regions free of areas of interest.

7. A system for an imaging device; comprising:
   a controller with instructions stored on non-transitory memory thereof that when executed cause the controller to:
      acquire tomosynthesis projection data;
      identify areas of interest in a plurality of slices reconstructed from the tomosynthesis projection data via a reconstruction algorithm;
      shape one or more first slabs to capture data in the plurality of slices a threshold distance away from each of the areas of interest; and
      shape one or more second slabs to capture data in the plurality of slices within the threshold distance of each of the areas of interest, the threshold distance measured along a three-dimensional axis system including an x-axis, a y-axis, and a z-axis;
      wherein at least one of the one or more first slabs or one or more second slabs has a non-uniform thickness, and wherein at least one of the one or more first slabs or one or more second slabs is curved, such that the one or more first slabs and the one or more second slabs include two curved slabs with curves that are complementary to one another.

8. The system of claim 7, wherein the instructions further cause the controller to maximize a thickness of one or more third slabs in response to areas of interest not being identified.

9. The system of claim 7, wherein the instructions further cause the controller to minimize a thickness of the one or more second slabs.

10. The system of claim 7, wherein the instructions further cause the controller to shape a first slab of the one or more first slabs to include a portion of a first slice of the plurality of slices free of an area of interest, and wherein the instructions further cause the controller to shape a second slab of the one or more second slabs to include a remaining portion of the first slice of the plurality of slices comprising the area of interest.

11. The system of claim 7, wherein a single slab of the one or more second slabs includes two or more of the areas of interest in response to the two or more of the areas of interest being within the threshold distance of each other.

12. The system of claim 7, wherein one of the one or more second slabs includes a first area of interest and another of the one or more second slabs includes a second area of interest, and wherein a distance between the first area of interest and the second area of interest is greater than the threshold distance.

13. A system for generating an image from a multi-dimensional image data set, comprising:
 a controller with instructions stored on non-transitory memory thereof that when executed cause the controller to:
  obtain a volume of image data, the volume of image data including a plurality of slices, each of the plurality of slices separated along a z-axis normal to an x-y plane;
  identify areas of interest in the plurality of slices; and
  reconstructing a series of slab images by dividing the plurality of slices into a plurality of slabs based on locations of the areas of interest, wherein one or more slabs of the plurality of slabs is curved, wherein each of the areas of interest is arranged in one curved slab of the plurality of slabs, and wherein the one curved slab is curved to be within a threshold distance of each of the areas of interest.

14. The system of claim 13, wherein data from a slice of the plurality of slices comprising an area of interest is divided into a first slab and a second slab of the plurality of slabs, and wherein the first slab comprises data from a portion of the slice the threshold distance away from the area of interest and the second slab comprises data from a portion of the slice within the threshold distance of the area of interest.

15. The system of claim 14, wherein the threshold distance is adjustable based on a breast thickness.

16. The system of claim 13, wherein different slabs of the plurality of slabs comprising different areas of interest are separated by slabs free of areas of interest.

\* \* \* \* \*